United States Patent [19]

Vann, III

[11] Patent Number: 4,941,897

[45] Date of Patent: Jul. 17, 1990

[54] MICROPOROUS FILTER AND METHOD

[75] Inventor: Clifton B. Vann, III, Charlotte, N.C.

[73] Assignee: L & H Technologies, Inc., Charlotte, N.C.

[21] Appl. No.: 117,667

[22] Filed: Nov. 5, 1987

[51] Int. Cl.[5] ............................................. B01D 53/22
[52] U.S. Cl. ..................................... 55/158; 55/310;
55/420; 55/480; 55/504; 55/528; 210/321.89;
210/500.23
[58] Field of Search ................... 55/97, 158, 310, 311,
55/420, 480, 503–506, 508, 512, 514, 527, 528,
16; 210/500.23, 500.28, 500.33, 500.36, 321.87,
321.89

[56]  References Cited

U.S. PATENT DOCUMENTS

| 3,390,514 | 7/1968 | Raschke | 55/311 X |
| 3,478,497 | 11/1969 | Doig et al. | 55/508 X |
| 3,505,794 | 4/1970 | Nutter et al. | 55/527 X |
| 3,832,830 | 9/1974 | Gerow | 55/158 |
| 4,020,230 | 4/1977 | Mahoney et al. | 55/527 X |
| 4,334,993 | 6/1982 | Norton | 55/158 X |
| 4,364,759 | 12/1982 | Brooks et al. | 55/487 |
| 4,401,567 | 8/1983 | Shindo et al. | 210/500.23 X |
| 4,405,688 | 9/1983 | Lowery et al. | 428/398 |
| 4,493,716 | 1/1985 | Swick | 55/16 X |
| 4,531,954 | 7/1985 | Klein | 55/159 |
| 4,557,955 | 12/1985 | Walch et al. | 55/528 X |
| 4,568,366 | 2/1986 | Frederick et al. | 55/159 |
| 4,636,307 | 1/1987 | Inoue et al. | 55/159 X |
| 4,640,773 | 2/1987 | Nishida et al. | 55/158 X |
| 4,647,377 | 3/1987 | Miura | 210/500.23 X |
| 4,666,543 | 5/1987 | Kawano | 210/500.23 X |
| 4,668,401 | 5/1987 | Okumura et al. | 55/16 X |
| 4,707,267 | 11/1987 | Johnson | 55/158 X |
| 4,729,773 | 3/1988 | Shirato et al. | 55/159 X |
| 4,750,918 | 6/1988 | Sirkar | 55/16 |

FOREIGN PATENT DOCUMENTS

| 217335 | 4/1987 | European Pat. Off. | 210/500.23 |
| 3205229 | 8/1983 | Fed. Rep. of Germany | 55/158 |
| 61-254292 | of 0000 | Japan . | |
| 61-274707 | of 0000 | Japan . | |
| 102292 | 8/1979 | Japan | 55/158 |
| 68007 | 4/1985 | Japan | 210/500.23 |
| 142860 | 7/1985 | Japan | 210/500.36 |
| 147202 | 8/1985 | Japan | 210/500.23 |
| 146308 | 7/1986 | Japan | 210/500.23 |
| 192308 | 8/1986 | Japan | 55/158 |
| 247606 | 11/1986 | Japan | 55/158 |
| 38220 | 2/1987 | Japan | 55/158 |
| 74434 | 4/1987 | Japan | 55/158 |

OTHER PUBLICATIONS

WO86/02914, Leonard et al., published 5/22/86.
"Technical Information, Fabrication & Handling—Hollow Fiber", Celanese Bulletin, Mar., 1985.
Liquid-Liquid Extractions with Microporous Hollow Fibers (Nancy D'Ella, Lise Dahuron and E. L. Cussler-)—Journal of Membrane Science, (1986), 309-319.

Primary Examiner—Robert Spitzer
Attorney, Agent, or Firm—W. Thad Adams, III

[57] ABSTRACT

A filter for removing micron and sub-micron molecular-sized particulate matter from a moving gas stream and comprising an enclosed filter module having a gas inlet for being connected to a source of gas to be filtered and gas outlet for discharging filtered gas from the module. A filter element is positioned in the filter module in gas flow interposed relation downstream of the gas inlet and upstream of the gas outlet in such manner that the gas must pass through the filter element in order to reach the gas outlet. The filter element comprises a multiplicity of hollow fibers each defined by a membrane wall formed of a microporous material surrounding a centrally-disposed lumen wherein filtration occurs by passing the gas from an upstream side of the hollow fiber through the membrane wall of the fibers to a downstream side thereof.

12 Claims, 6 Drawing Sheets

MICROPOROUS FILTER AND METHOD

TECHNICAL FIELD AND BACKGROUND OF THE INVENTION

This invention relates to a microporous particulate filter capable of removing micron, sub-micron and molecular particulate from a pressurized continuous gas stream. The filter has a wide range of application in the medical and dental fields, food industry and in the manufacture of electronics.

The importance of air and medical and dental gas has become a much more critical consideration in the recent past as a result of the development of Acquired Immunodeficiency Syndrome (AIDS) as a serious public health concern. Since the method of transmission is still incompletely understood, any means by which air or any other gas contaminated with AIDS or another infectious disease comes into contact with the bloodstream of a patient must be carefully scrutinized to reduce the possibility that the infection is being inadvertently transmitted.

The invention has a particular application to the filtration of bacteria and viruses from gases. For example, in medical and dental fields the filter has application in the centralized and point of use filtration of medical air and gas streams used in respiration therapy, in the filtration and collection of potentially harmful infectious particulate from vacuum system effluent discharge, and in centralized and point of use filtration of anesthesia gas streams.

Filtration removes potentially harmful particulate which if left unfiltered could increase risk of patient infection. The integral nature of the filter disclosed in this application reduces the possibility that improper handling and disposal of the effluent discharge can cause disease transmission.

In dental applications, there is a perceived danger from circulation, compression and reuse of air directed into the mouth of a patient, where contaminants may enter the bloodstream. The problem is aggravated because compression of unfiltered atmospheric air from within the dental environment has the effect of concentrating any contaminants present. Filtration of the air within a medical or dental environment also removes potentially abrasive particulate matter which could damage internal working parts of instruments, thereby shortening their working life.

In the food industry, filtration of solids and potentially infectious particulate from compressed air used in processing and dispensing food and beverages reduces the possibility of contamination by contact between the food and the air.

In the electronics industry, removal of micron and sub-micron particles from atmospheric air reduces possibility of these particles contaminating semiconductor and similar components.

The preferred filter medium used in the filter disclosed in this application is a microporous hollow fiber such as Celgard (TM) microporous hollow fiber manufactured by Questar division of Celanese Corporation. Technical information, fabrication and handling information concerning this fiber can be found in a Celanese bulletin entitled *Technical Information, Fabrication & Handling—Hollow Fiber*, March, 1985. This fiber is formed of polypropylene polyolefin resins. This product has heretofore been used in electrochemical systems, batteries, electronic devices, sterile packaging, medical devices and a variety of industrial and biotechnical applications, as well as supports in immobilized liquid and thin film membranes. The hollow fiber offers controlled and relatively uniform porosity as compared with asymmetric ultrafiltration/microfiltration membranes. The fiber is resistant to acids and bases and is permeable to gases and vapors. The geometry of the hollow fiber offers a compact size because of the high membrane surface area-to-volume ratio. The fiber resists fouling due to shear forces generated during flow through the fiber lumen and is self-supporting.

The fiber surface is comprised of a series of parallel slot-like pores. These pores form tortuous, interconnected channels leading from one surface of the fiber to the other. The pores allow the flow of gases and vapors but block passage of many bacteria, colloids and other sub-micron particles and solutes. The pore structure of the fiber is relatively uniform and homogeneous from one side of the fiber wall to the other. This is in contrast to asymmetric membranes wherein the pore width increases by orders of magnitude as it progresses from side of the membrane to the other.

Because this fiber is known to pass vapors while blocking passages of liquids, it has heretofore been used to separate blood proteins, macromolecules and cellular material from blood, and to infiltrate oxygen into blood in blood oxygenators. It has also been applied to pollution control problems and recovery of byproducts. Insofar as is known, the fiber has not been heretofore used to filter sub-micron and molecular matter from gases, such as air and medical/dental gases.

Many viruses have a size much smaller than the average pore width of the hollow fiber—0.04–0.05 microns. Polio virus, because of its extremely small size is considered a good test of the ability of a filter material to filter viruses. Surprisingly, it has been determined by laboratory analysis that polio virus is filtered to an extremely high degree of efficiency by the hollow fiber used in the present invention. This is believed to be caused not only by the tortuous, three-dimensional path through the fiber wall but by an affinity of the fiber for the matter which impacts the side walls of the pores as it transits the pores from one side of the fiber wall membrane to the other.

This invention makes effective use of the characteristics of the hollow fiber in combination with a mechanical system which permits safe operation and disposal of the filter.

SUMMARY OF THE INVENTION

Therefore, it is an object of the invention to provide a microporous filter which will filter micro and molecular sized particles from a moving gas stream.

It is another object of the invention to provide a microporous filter which will filter viruses and other contaminants from air and medical/dental gases.

It is yet another object of the invention to provide a filter which is safe to operate and dispose of after use.

These and other objects of the present invention are achieved in the preferred embodiments disclosed below by providing a filter for removing micron and submicron molecular-sized particulate matter from a moving gas stream. The filter preferably comprises an enclosed filter module having a gas inlet for being connected to a source of gas to be filtered and a gas outlet for discharging filtered gas from the module. A filter element is positioned in the filter module in gas flow interposed relation downstream of the gas inlet and upstream of the gas outlet in such manner that the gas must pass through the filter element in order to reach the gas outlet. The filter element comprises a membrane wall formed of a microporous material wherein filtration occurs by passing the gas from an upstream side of the membrane wall to a downstream side thereof.

Preferably, the filter element comprises a multiplicity of hollow fibers, each fiber being defined by a membrane wall formed of a microporous material surrounding a centrally-disposed lumen. Filtration occurs by passing the gas from an upstream side of the hollow fiber through the membrane wall of the fibers to a downstream side thereof.

According to one preferred embodiment of the invention, the gas flow is through the membrane wall of the fibers downstream into the lumen.

According to another preferred embodiment of the invention, the gas flow is through the membrane wall from the lumen downstream to the exterior of the fiber.

According to yet another embodiment of the invention, the membrane comprises a flat sheet.

The hollow fibers comprise a polymer and the pores in the membrane wall define a three-dimensional tortuous flow path from one surface to the other to trap and thereby filter particulate matter smaller than the nominal size of the pores.

Preferably, the fiber comprises polypropylene.

According to another preferred embodiment of the invention, a filter is provided for removing micron and sub-micron molecular-sized particulate matter from a moving gas stream and comprises a base having a base gas inlet for being connected to a source of gas to be filtered and a base gas outlet for discharging filtered gas.

An enclosed, replaceable and disposable filter module is releasably received in and supported by the base. The filter module has a module gas inlet adapted for sealing gas flow connection to the base gas inlet, and a module gas outlet adapted for sealing gas flow connection to the base gas outlet for discharging filtered gas from the module and base.

A filter element is sealingly positioned in the filter module in gas flow interposed relation downstream of the module gas inlet and upstream of the module gas outlet in such manner that the gas must pass through the filter element in order to reach the module gas outlet. The filter element comprises a multiplicity of hollow fibers, each defined by a membrane wall formed of a microporous material surrounding a centrally-disposed lumen. Filtration occurs by passing the gas from an upstream side of the hollow fiber through the membrane wall of the fibers to a downstream side thereof.

Preferably, the base includes a pressure relief valve for permitting pressure within the filter module to be equalized to atmospheric pressure for removal and disposal of the filter module.

According to one preferred embodiment of the invention, the filter module is cylindrical, and the module gas outlet is concentrically positioned in one end of the filter module and the module gas inlet is eccentrically positioned in the same one end of the filter module for preventing installation of the filter module in the base in the reverse gas flow direction.

Preferably, the multiplicity of hollow fibers are grouped in a dense bundle aligned on the same longitudinal axis wherein the fibers are held within the filter module by one end of the bundle.

According to a preferred embodiment of the invention, the fibers are held in bundle form by potting one end of the bundle to form a disc-like structure sealing the spaces between the individual fibers while exposing the lumen for gas flow therethrough into the module gas outlet.

Preferably, the filter module includes a check valve cooperating with the module air inlet for preventing unfiltered gas on the upstream side of the filter element from escaping into the atmosphere during and after replacement of the filter module.

According to another preferred embodiment of the invention, the base includes a threaded end cap for being tightened against the filter module and urging the filter module into sealing engagement with the base, and for being loosened and removed to remove and replace the filter module.

Preferably, the fiber bundle is suspended from one end thereof in the filter module in spaced-apart relation to the inner walls of the filter module for free gas flow around all sides and the non-suspended end of the fiber bundle.

In accordance with the method of the invention, the method steps include providing a filter element sealingly positioned in a filter module intermediate a gas inlet and a gas outlet, the filter element comprising a membrane wall formed of a microporous material wherein filtration occurs by passing the gas from an upstream side of the membrane wall to a downstream side thereof; and passing a gas containing micron and sub-micron molecular-sized particulate matter into the filter module and through the filter from one side to the other under pressure, thereby filtering the particulate matter therefrom.

Preferably, the filter element comprises a multiplicity of hollow fibers each defined by a membrane wall formed of a microporous material surrounding a centrally-disposed lumen wherein filtration occurs by passing the gas from an upstream side of the hollow fibers through the membrane wall of the fibers to a downstream side thereof.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENT

Figure 1:
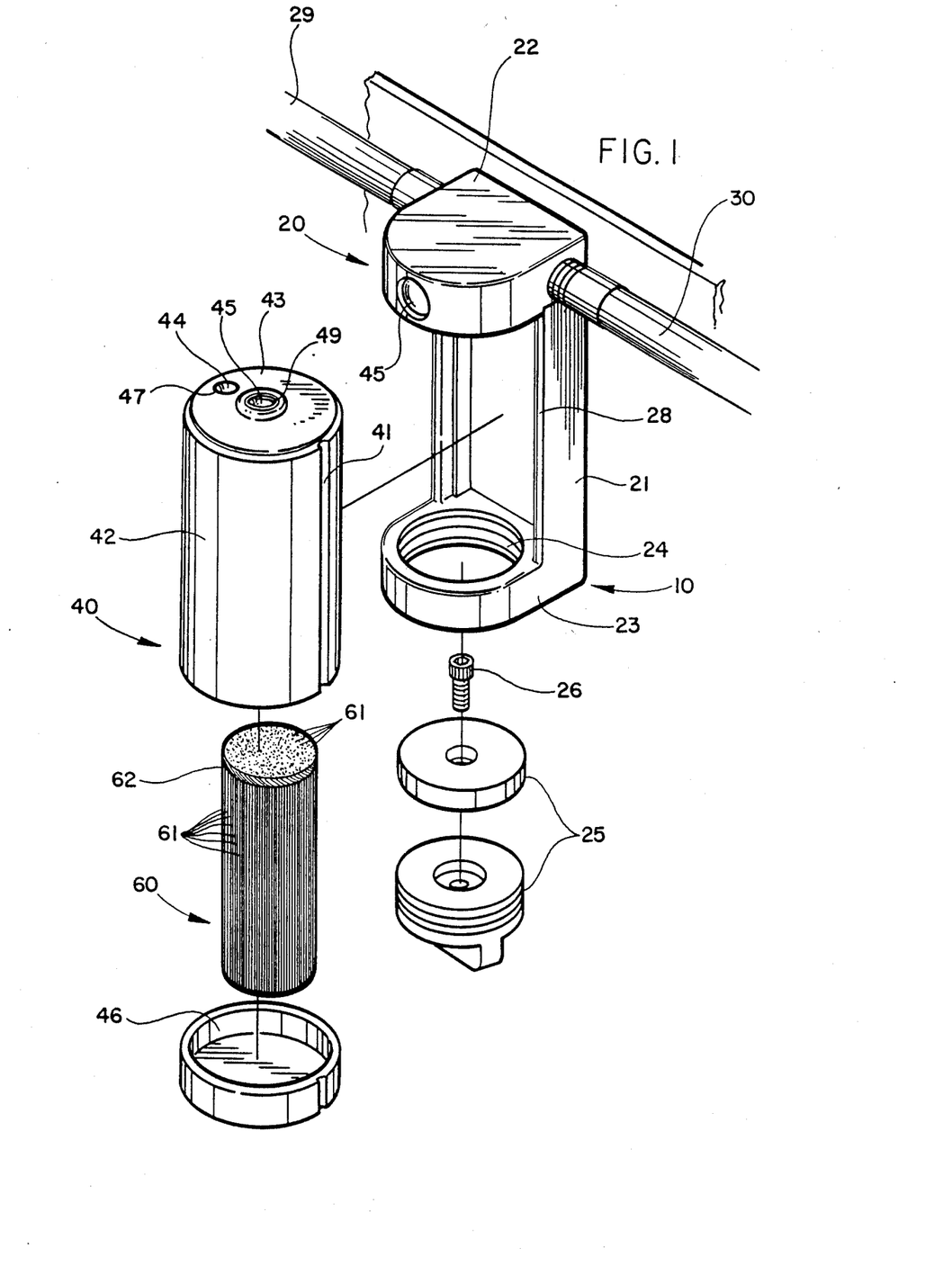
FIG. 1 is an exploded view of the filter according to the present invention.

Referring now specifically to the drawings, a filter according to the present invention is illustrated in FIG. 1 and shown generally at reference numeral 10. The filter 10 is comprised of three basic parts—a base 20, and filter module 40 and a filter element 60. The filter element 60 is sealed within filter module 40 and both parts are together disposable after the filtration capacity of the filter element 60 has been exhausted. Filter module 40 is positioned in the base 20 and thereby interconnects with a gas supply.

More specifically, base 20 comprises a housing 21 intended to be suitably mounted on a wall, cabinet or some other surface. A top holder 22 receives filter module 40 in a manner to be described more specifically below. A bottom holder 23 defines an annular threaded opening 24 which receives a two piece end cap 25 connected by a bolt 26. The space between the top holder 22 and bottom holder 23 defines an area into which fits filter module 40. Filter module 40 is inserted laterally into the area after which end cap 25 is tightened. Proper rotational alignment of the filter module 40 in the base 20 is achieved by mating an elongate groove 41 in the outer surface of filter module 40 against the longitudinally-extending edge 28 of housing 21.

Gas supply and gas exhaust conduits 29, 30 are interconnected into top holder 22 on opposite sides thereof. Base 20 may be constructed of various materials including, for example, aluminum, brass, stainless steel or various FDA approved plastics.

Filter module 40 comprises a cylindrical body 42, the top end of which is sealed by a top cap 43. Top cap 43 includes a gas inlet 44 eccentric to filter module body 42 and a gas outlet 45 concentric with filter module body 42. The filter element 60 is installed into the filter module 40 through the bottom opening, after which the bottom opening is permanently sealed closed by a bottom cap 46. Gas inlet 44 and gas outlet 45 are provided with rubber O-ring seals 47, 49, respectively, and seal against mating surfaces of the top holder 22, as is more particularly described below.

Figures 2, 3:
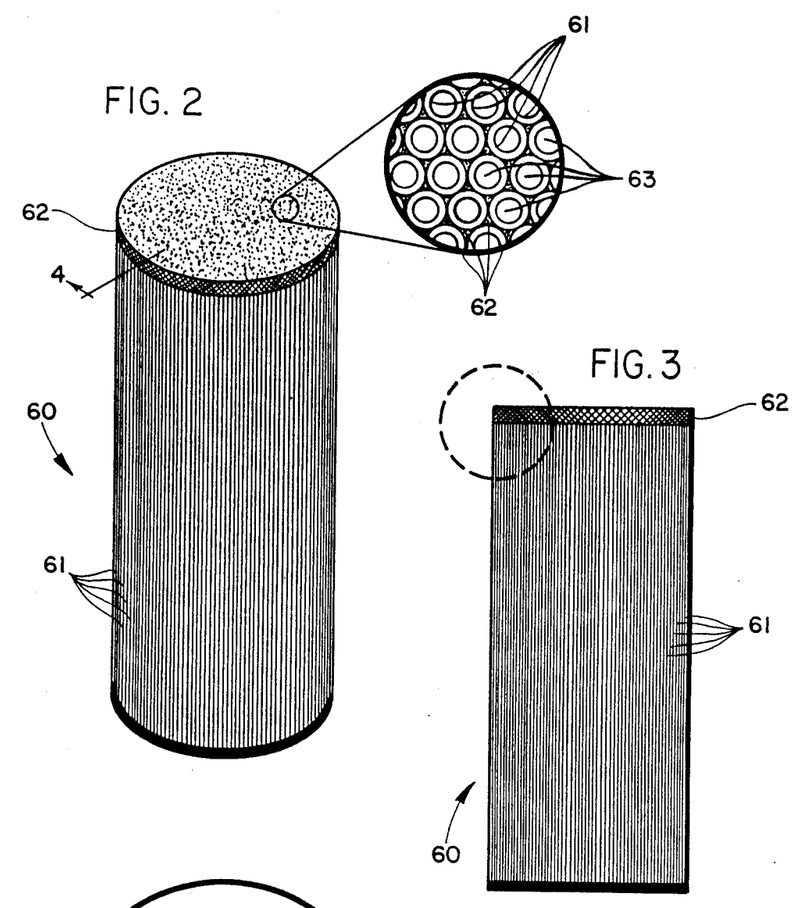
FIG. 2 is a perspective view of the fiber bundle, with a fragmentary enlargement of a small section of the top surface of the bundle.
FIG. 3 is a side elevation view of the fiber bundle shown in FIG. 2.
Figure 4:
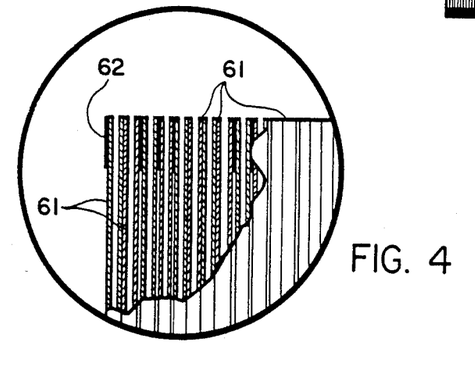
FIG. 4 is a fragmentary, enlarged cross-section of the circled section shown in FIG. 3.

Referring now to FIGS. 2, 3 and 4, the filter element 60 is described in further detail. To be usable, the fiber bundle must be potted on one end to provide a sealed area between the outside and the lumen of the fibers. As is shown in FIGS. 2, 3 and 4, filter element 60 is comprised of a multiplicity of individual fibers 61, which may be of various porosities and sizes based upon considerations of rate of gas flow through the filter, particulate size and the like. The filter element 60 is typically packed to a density of 40%. The filter element is formed into a bundle arranging the fibers in a coherent, parallel array and then potting one end of all of the fibers into a bed of polyurethane resin 62. Full details regarding this process can be found on page seven of the publication referred to above, entitled *Technical Information, Fabrication & Handling—Hollow Fiber*, March, 1985. After the resin is at least partially cured, the top layer of the resin 62 is sliced off, leaving a surface with exposed, open fibers 61 with the spaces between the fibers filled in with the resin 62. This is best shown in FIG. 2. The potting not only secures the fibers 61 into the required bundle, but the cured resin also supports the individual fibers with the lumens 63 (the hollow, central core of the fiber) in an open, substantially cylindrical configuration. The resin 62 also prevents collapsing of the fiber walls. Of course, the opposite end of the filter element is sealed to prevent gas flow through the end of the fibers.

The enlarged view shown in FIG. 2 is an idealized one, but nevertheless illustrates that the fibers 61 are secured together into an array. The view in FIG. 4 illustrates that a cross-section through the resin 62 would reveal an irregular arrangement of the fibers 61, which are nevertheless securely attached together in sealing relation.

Figure 5:
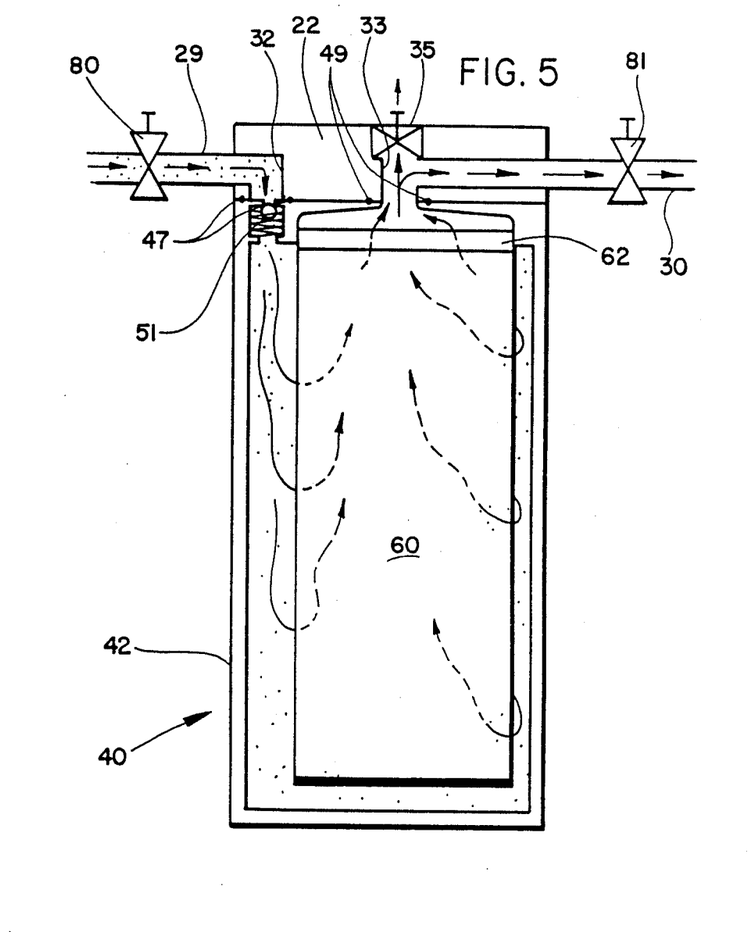
FIG. 5 is a schematic view of the filter showing the flow path of gases therethrough.
Figure 8:
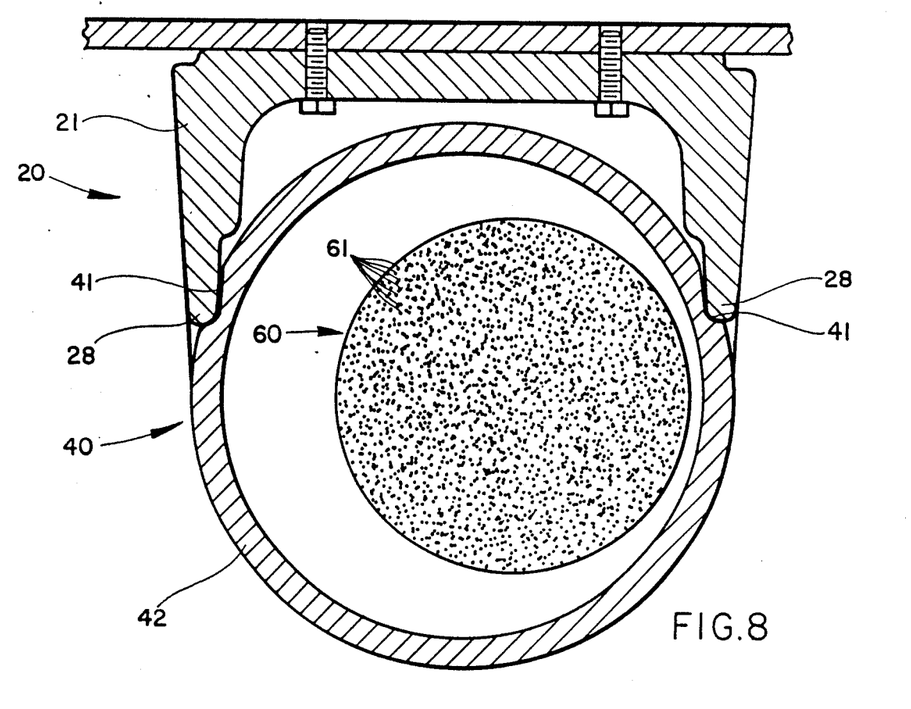
FIG. 8 is a horizontal cross-section of the filter showing the eccentric relation of the fiber bundle to the cylindrical filter module.

Referring now to FIG. 5, the simplified cross-section illustrates that the gas inlet 44 mates with a gas inlet 32 in top holder 22, and that gas outlet 45 mates with a gas outlet 33 in top holder 22. Filter element 60 is sealingly attached to the top 43 of filter module 40 in surrounding relation to gas outlet 45. The filter element 60 is asymmetrically arranged in the filter module 40 to provide room for gas inlet 44 and to permit adequate room for gas circulation and diffusion within filter module 40. See also FIG. 8. A pressure responsive check valve 51 is installed in filter module 40 in gas inlet 44. Check valve 51 is open only when gas under pressure is flowing through the valve. Any loss of pressure seals the interior of the filter module 40 against leakage of contaminated air into the environment.

Figure 9:
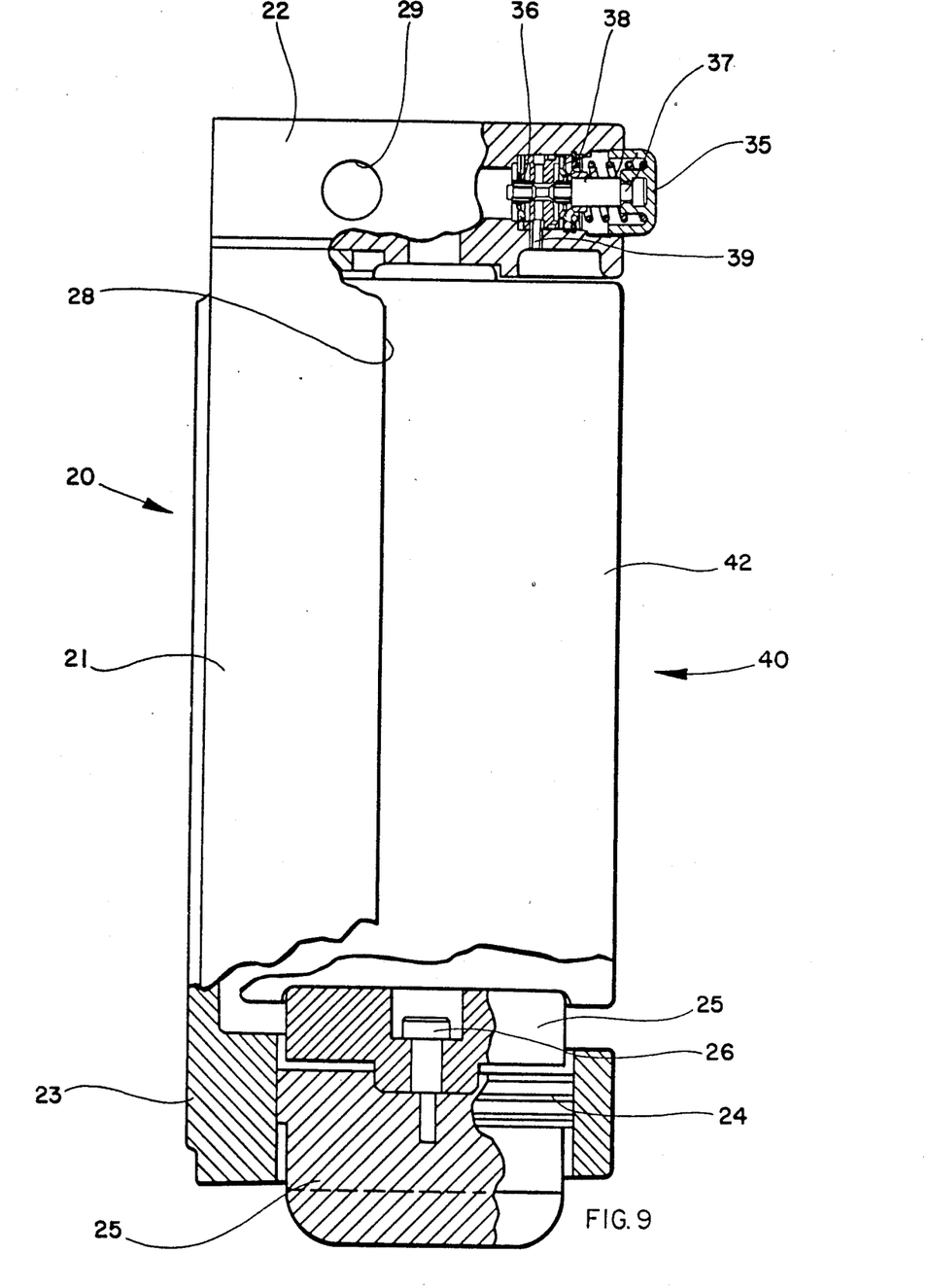
FIG. 9 is a fragmentary vertical cross-section, with parts broken away, of the filter.

As is also shown in FIG. 5 and also FIG. 9, top holder 22 includes a pressure relief valve 35 which, upon activation, releases pressure within filter module 40 and equalizes the pressure inside filter module 40 with the outside environment. Shutoff valves 80 and 81 are not part of the invention per se, but enable the filter module 40 to be isolated from the contaminated and filtered air before removal and replacement.

Figure 6:
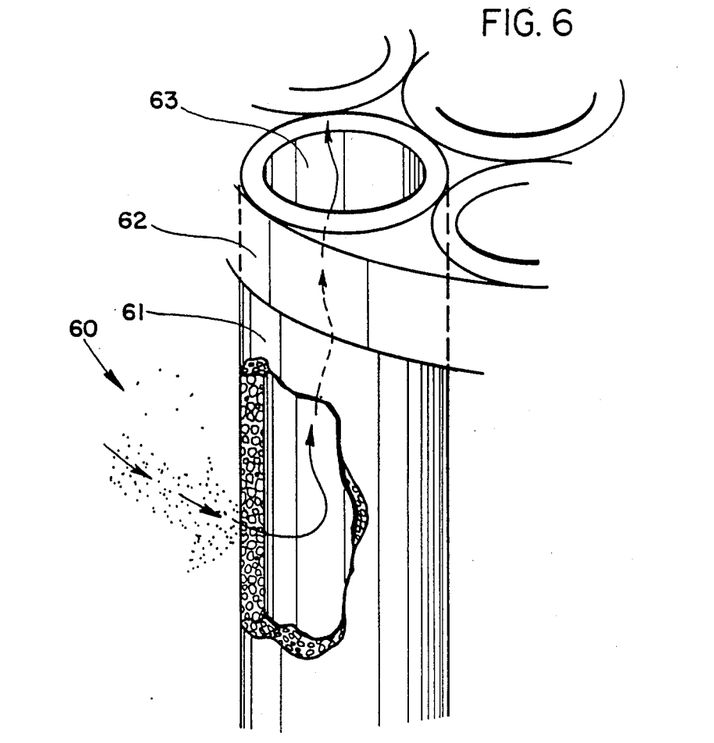
FIG. 6 is an extreme fragmentary enlargement of a segment of the fiber bundle showing the path of the gas through the side wall of the fiber.
Figure 7:
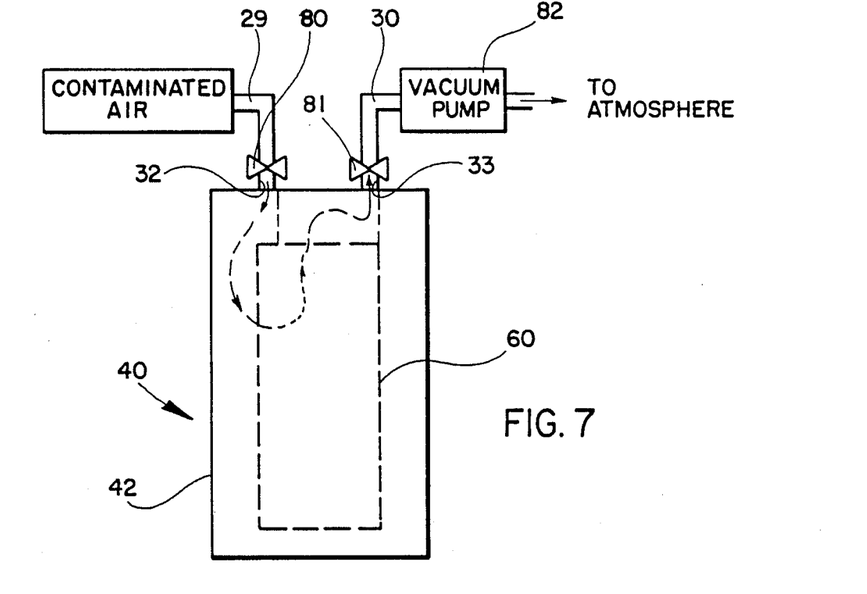
FIG. 7 is a schematic view of the filter in combination with a valving arrangement useful in changing filter modules.

The physical characteristics of the fibers 61 have been described in detail above. By reference to FIG. 6, the basic flow pattern of a gas through a fiber is shown. As described above, each fiber has a wall thickness through which the pores define tortuous path. The twists and turns in the path provide tight corners, kinks and areas of reduced diameter which trap particles of a much smaller size than the nominal pore size in the fiber. In the view shown in FIG. 6, the flow is from the outside of the fiber 61 through the side wall and into the lumen 63. An arrangement to accomplish this flow pattern is shown in FIG. 7, where a vacuum pump 82 creates a negative pressure through the filter element 60 from the upstream to the downstream side of the fibers 61. A positive pressure pump could also be used on the upstream side to force gas through the filter element 60. In addition, gas flow can be reversed, so that contaminated air is passed into the lumen 63 of the fibers 61 whereby filtration takes place as the gas passes to the outside of the fibers 61. The unique, uniform pore size from one side of the fiber walls to the other permit the filtration to occur in either direction.

Determining the frequency with which the filter module 40 should be changed can be accomplished by metering the gas filtered through the filter 10, or simply replacing the filter module at predetermined time intervals. To change the filter module, pressure must first be equalized between the interior of the filter module and the outside environment. Referring again to FIG. 5, valve 80 is first closed to discontinue the flow of contaminated gas. This will also close check valve 51, sealing the filter module and preventing contaminated air from escaping through inlet 44. Continued negative pressure on the downstream side of the filter pulls residual contaminated air through the filter element. Then, valve 81 is closed, discontinuing pressure on the downstream side of the filter element. Pressure, either negative or positive, is therefore trapped in the filter module 40. Pressure relief valve 35 is depressed, equalizing pressure. The positive pressure trapped in filter module 40 is released downstream from the filter element. Therefore, the vented gas is filtered, not contaminated, gas.

Pressure relief valve 35 is preferably a Humphrey Products Model No. 125 INS-P2-10 cartridge valve which will operate in a 2-way or 3-way mode. As is shown in FIG. 9, pressure entering the bottom of the valve holds the valve in a closed position with the bottom diaphragm 36 seated. Force on top of the main stem 37 unseats the bottom diaphragm 36 and lowers top diaphragm 38 into its conical seat, sealing off the exhaust. Gas flows through perforations in the bottom diaphragm 36, past the seat and out through a cross-drilled port which communicates with a port 39 in top holder 22. After release of pressure in filter module 40, end cap 25 is unscrewed. This permits filter module 40 to slide down in the housing 21 far enough to clear top holder 22. Then, filter module 40 is removed from housing 21 by grasping it and pulling it laterally outwardly. Note according to FIG. 1 that the groove 41 in the side wall of filter module 40 slides along edge 28 of housing 21 and maintains proper alignment between these two elements. This is essential in order for gas inlet 44 and gas outlet 45 to seat properly. The entire filter module 40 is disposed of.

A new filter element 40 is installed by aligning groove 41 with the edge 28 and inserting the filter module 40 laterally into housing 21. After insuring that the filter module 40 is properly mated, end cap 25 is tightened. Pressure exerted by the end cap 25 presses the O-rings 47 and 49 against the gas inlet 32 and gas outlet 33, respectively, of top holder 22.

A method and apparatus for microfiltration of gases is described above. Various details of the invention may be changed without departing from its scope. Furthermore, the foregoing description of the preferred embodiment according to the present invention is provided for the purpose of illustration only and not for the purpose of limitation—the invention being defined by the claims.

I claim:

1. A filter for removing micron and sub-micron molecular-sized particulate matter from a moving gas stream, comprising:
   (a) a base having a base gas inlet for being connected to a source of gas to be filtered and a base gas outlet for discharging filtered gas;
   (b) an enclosed replaceable and disposable cylindrical filter module for being releasably received in and supported by said base, said filter module having a module gas inlet adapted for sealing gas flow connection to said base gas inlet, and a module gas outlet adapted for sealing gas flow connection to said base gas outlet for discharging filtered gas from the module and base; wherein one of said module gas outlet and said module gas inlet is concentrically positioned in one end of said filter module and the other of said module gas inlet and module gas outlet is eccentrically positioned in the same one end of said filter module for preventing installation of said filter module in said base in reverse gas flow direction; and
   (c) a filter element sealingly positioned in said filter module in gas flow interposed relation downstream of said module gas inlet and upstream of said module gas outlet in such manner that the gas must pass through said filter element in order to reach said module gas outlet, said filter element comprising a multiplicity of hollow fibers each defined by a membrane wall formed of a microporous material surrounding a centrally-disposed lumen wherein filtration occurs by passing the gas from an upstream side of the hollow fiber through the membrane wall of the fibers to a downstream side thereof, said filter element comprising a multiplicity of hollow fibers each defined by a membrane wall formed of a microporous material surrounding a centrally-disposed lumen wherein filtration occurs by passing the gas from an upstream side of the hollow fiber through the membrane wall of the fibers to a downstream side thereof.

2. A filter according to claim 1, wherein said gas flow is through the membrane wall of the fibers downstream into the lumen.

3. A filter according to claim 1, wherein said gas flow is through the membrane wall from the lumen downstream to the exterior of the fiber.

4. A filter according to claim 1, wherein said fiber comprises polypropylene.

5. A filter according to claim 1, wherein said base includes a pressure relief valve for permitting pressure within said filter module to be equalized to atmospheric pressure for removal and disposal of said filter module.

6. A filter according to claim 1, wherein said multiplicity of hollow fibers are grouped in a dense bundle of fibers aligned on the same longitudinal axis and wherein said fibers are held within said filter module by one end of said bundle.

7. A filter according to claim 6, wherein said fiber bundle is held in bundle form by potting the one end of the bundle to form a disc-like structure sealing the spaces between the individual fibers while exposing the lumen for gas flow therethrough into said module gas outlet.

8. A filter according to claim 7, wherein said fiber bundle is suspended from one end thereof in said filter module in spaced-apart relation to the inner walls of the filter module for free gas flow around all sides and the other end of the fiber bundle.

9. A filter according to claim 6, wherein said hollow fibers comprise polypropylene.

10. A filter according to claim 6 or 7, wherein said filter module includes a check valve cooperating with said module air inlet for preventing unfiltered gas on the upstream side of said filter element from escaping into the atmosphere during and after replacement of said filter module.

11. A filter according to claim 10, wherein said base includes a threaded end cap for being tightened against said filter module and urging said filter module into sealing engagement with said base, and for being loosened and removed to remove and replace said filter module.

12. A filter according to claim 1, wherein the average pore size width of the pores in the membrane is 0.03 to 0.05 microns.

* * * * *

Disclaimer 4,941,897.—*Clifton B. Vann, III*, Charlotte, N.C. MICROPOROUS FILTER AND METHOD. Patent dated July 17, 1990. Disclaimer filed Feb. 6, 1991, by the assignee, L & H Technologies, Inc.

The term of this patent subsequent to Apr. 4, 2006, has been disclaimed.
[ *Official Gazette May 14, 1991* ]